US007928204B2

(12) United States Patent
Mangold et al.

(10) Patent No.: US 7,928,204 B2
(45) Date of Patent: *Apr. 19, 2011

(54) SPORE SPECIFIC ANTIGEN

(75) Inventors: Beverly L. Mangold, Rockville, MD (US); Jennifer L. Aldrich, Frederick, MD (US); William Max Nelson, Potomac, MD (US)

(73) Assignee: Tetracore, Inc., Rockville, MD (US)

( * ) Notice: Subject to any disclaimer, the term of this patent is extended or adjusted under 35 U.S.C. 154(b) by 892 days.

This patent is subject to a terminal disclaimer.

(21) Appl. No.: 11/234,752

(22) Filed: Sep. 23, 2005

(65) Prior Publication Data

US 2007/0231840 A1 Oct. 4, 2007

Related U.S. Application Data

(63) Continuation-in-part of application No. 11/127,435, filed on May 11, 2005, now Pat. No. 7,772,374.

(60) Provisional application No. 60/570,798, filed on May 12, 2004.

(51) Int. Cl.
*C07K 16/00* (2006.01)

(52) U.S. Cl. .................................. 530/388.1; 530/388.2

(58) Field of Classification Search ........................ None
See application file for complete search history.

(56) References Cited

U.S. PATENT DOCUMENTS 6,913,756 B1 7/2005 Kearney

FOREIGN PATENT DOCUMENTS

| WO | WO0183561 A2 * | 11/2001 |
| WO | WO 03/103481 | 12/2003 |

OTHER PUBLICATIONS sequence alignment AC# Q9K3E4 , see under result 12.*
Fox et al. Journal of Microbiological Methods vol. 54. pp. 143-152, 2003.*
Hill, Karen K., et al. "Fluorescent Amplified Fragment Length Polymorphism Analysis of *Bacillus anthracis*, *Bacillus cereus*, and *Bacillus thuringiensis* Isolates", *Applied and Environmental Microbiology* (2004) 70(2):1068-1080.
Hoffmaster, Alex R., et al. Identification of anthrax toxin genes in a *Bacillus cereus* associated with an illness resembling inhalation anthrax, *PNAS* (2004) 101(22):8449-8454.
Chen, Yinghua, et al. "A Novel Spore Peptidoglycan Hyrolase of *Bacillus cereus*: Biochemical Characterization and Nucleotide Sequence of the Corresponding Gene, *sleL*" *Journal of Bacteriology* (2000) 182(6):1499-1506.
Shimamoto, Seiko, et al. "Partial Characterization of an Enzyme Fraction with Protease Activity Which Converts the Spore Peptidoglycan Hydrolase (SleC) Precursor to an Active Enzyme during Germination of *Clostridium perfringens* S40 Spores and Analysis of a Gene Cluster Involved in the Activity", *Journal of Bacteriology* (2001) 183(12):3742-3751.
Chen, Yinghua, et al. "Molecular Characterization of a Germination-Specific Muramidase from *Clostridium perfringens* S40 Spores and Nucleotide Sequence of the Corresponding Gene", *Journal of Bacteriology* (1997) 179(10):3181-3187.
Keim, P., et al. "Multiple-Locus Variable-Number Tandem Repeat Analysis Reveals Genetic Relationships within *Bacillus anthracis*", *Journal of Bacteriology* (2000) 182(10):2928-2936.
Brettin et al., Database GenBank NCBI; retrieved from http://www.ncbi.nlm.gov Database Accession No. YP_029658.
Creighton, ed., "Proteins: Structures and Molecular Principles" pp. 314-315 (1984).
Creighton, ed., "Protein Structure: A Practical Approach," pp. 184-186 (1989).
Dang et al., "Bacillus Spore Inactivation Methods Affect Detection Assays," Appl. Environ. Microbiol., 67(8):3665-3670 (2001).
Han et al., Database GenBank NCBI; retrieved from http://www.ncbi.nlm.gov Database Accession No. YP_037686 (2004).
Han et al., Database GenBank NCBI; retrieved from http://www.ncbi.nlm.gov, Database Accession No. YP_084899 (2005).
Lai et al., "Proteomic Analysis of the Spore Coats of *B. subtilis* and *B. anthracis*," J. Bacteriol., 185(4):1443-1454 (Feb., 2003).
Longchamp and Leighton, "Molecular Recognition Specificity of *B. anthracis* spore antibodies," J. Appl. Micro. 87:246-249 (1999).
Nosoh and Sekiguchi, eds.. "Protein Stability and Stabilization Through Protein Engineering," pp. 196-217 (1991).
Read et al., Database GenBank NCBI; retrieved from http://www.ncbi.nlm.gov, Database Accession No. ZP_00393845 (2005).
Todd et al., "Genes of *B. cereus* and *B. anthracis* Encoding Proteins of the Exosporium," J. Biol. 185(11): 3373-3378 (Jun. 2003).
Williams et al., "Surface Layer Protein EA1 is not a Component of *B. anthracis* spores but is a Persistent Contaminant in Spore Preparations," J. Bacter. 186:566-569 (Jan. 2004).

* cited by examiner

*Primary Examiner* — Gary B. Nickol
*Assistant Examiner* — Khatol Shahnan-Shah
(74) *Attorney, Agent, or Firm* — Patentique PLLC

(57) ABSTRACT

The invention relates to a *Bacillus* spore specific antigen. Compositions and methods relating to the antigen are provided along with antibodies against the antigen. The antigen is specific for *Bacillus* spores relative to the vegetative form of the cells. The antigen is detectable on ungerminated spores. The antibodies may be used to detect the presence of *Bacillus* spores by use of methods provided herein. The invention also relates to articles of manufacture as well as kits comprising the antibodies which may be used in the detection methods of the invention.

20 Claims, 4 Drawing Sheets

Figure 1

```
1   MIQIVTVRSGDSVYSLASKYGSTPDEIVKDNGLNPAETLVVGQALIVNTKGNNYYVQPGD  60
1   ............................................................  60
1   ............................................................  60
1   ............................................................  60
1   ............................T...............................  60
1   ............................................................  60
1   ............................................................  60

61  SLYRISQTYNVPLASLAKVNNLSLKSILHVGQQLYIPKGTKRAVESIAYLQPSTIPIKES  120
61  ............................................................  120
61  ............................................................  120
61  ............................................................  120
61  ............................................................  120
61  ..................................V.........................  120
61  ..................................V......T...................  120

121 LVNATRAINPFLTYLAYFSPEAKRDGTLKEPTETAKIANIATQGNTIPMLVITNIENGNF  180
121 ............................................................  180
121 ...S........................................................  180
121 ............................................................  180
121 ............................................................  180
121 ..........................................K.................  180
121 ..........................................K.................  180

181 SADLTSVILRDATIQNKFITNILQTAEKYGMRDIHFDFESVAPEDREAYNRFLRNVKTRL  240
181 ............................................................  240
181 ............................................................  240
181 ............................................................  240
181 ............................................................  240
181 ..................Q.........................................  240
181 ..................Q.........................................  240
1                                     ........................  30

241 PSGYTLSTTLVPKTSSNQKGKFFETHDYKAQGQIVDFVVIMTYDWGWQGGPPMAISPIGP  300
241 .......................A....................................  300
241 .N.....................A....................................  300
241 .N.....................A....................................  300
241 .N.....................A....................................  300
241 .......................A...............N...................  300
241 .......................A....................................  300
31  .......................A....................................  90

301 VKEVLQYAKSQMPPQKIMMGQNLYGFDWKLPFKEGNPPAKAISSVAAVALARKYNVPIRY  360
301 ............................................................  360
301 ............................................................  360
301 .........................Q.......V..........................  360
301 .........................Q..................................  360
301 .........................Q..................................  360
301 .........................Q.................T................  360
91  .........................Q..................................  150
```

Figure 1 (con't)

```
361  DFTAQAPHFNYFDENGVQHEVWFEDSRSVQSKFNLMKEQGIGGISYWKIGLPFPQNWRLL  420
361  ............................................................  420
361  ............................................................  420
361  .......................A..I.................................  420
361  ............................................................  420
361  ............................................................  420
361  ............................................................  420
151  ............................................................  210
```

```
421  VENFTITKKG  430        SEQ ID NO:1
421  ..........  430        Bt 97-27
421  ..........  430        Bc E33L ("ZK")
421  ..........  430        Bc 10987
421  ..........  430        Bc G9241
421  ..........  430        Bc IFO 13597
421  ..........  430        Bc 14579
211  ..........  219        Bt serovar israelensis ATCC 35646
```

SPORE SPECIFIC ANTIGEN

RELATED APPLICATIONS

This application is related to U.S. patent application Ser. No. 11/127,435, filed May 11, 2005, which claims benefit of priority to U.S. Provisional Patent Application 60/570,798, filed May 12, 2004. Both applications are hereby incorporated by reference in their entireties as if fully set forth.

FIELD OF THE INVENTION

This invention relates to a *Bacillus* spore specific antigen and fragments thereof. The invention provides polypeptides of the antigen, and fragments thereof, as well as compositions comprising the polypeptides. The antigen is detectable on the spores of *B. anthracis*, and the invention also relates to detecting the antigen, or fragments thereof, as an indicator of the presence of *B. anthracis* spore(s). The antigen, or fragments thereof, also may be used to generate antibodies that bind the antigen, or fragments thereof, as found on *Bacillus* spores, including *B. anthracis* spores.

BACKGROUND OF THE INVENTION

*Bacillus anthracis*, the causative agent of anthrax, is a spore-forming, Gram-positive, non-hemolytic, rod-shaped bacterium. Anthrax is primarily a zoonotic disease of herbivores; however, humans can naturally acquire this disease directly from contact with infected herbivores, or indirectly via their products, such as hair, wool, and hides. Spores are the usual infective form. Anthrax presents clinically as three distinct syndromes, depending on the route of infection: cutaneous, gastrointestinal, and inhalational disease. Cutaneous anthrax is the most common naturally occurring form in humans. However, inhalational anthrax, although seen only rarely in naturally acquired infections, would be the major concern in a situation involving the release of aerosolized spores. Such was demonstrated by the accidental release of aerosolized spores from Sverdlovsk in the former Soviet Union in 1979 (Meselsona et al 1994) and the intentional release of aerosolized spores in the anthrax letter attacks in the United States in October 2001 (Jernigan et al., 2001). The high level of mortality seen with inhalational anthrax can be mitigated by administration of the appropriate antibiotics within 24-48 hours of exposure. However, delays in administrating antibiotics beyond 24-48 hours of exposure generally results in death to individuals receiving a lethal dose of spores.

The spore coat and exosporium of *B. anthracis* have been the focus of previous studies. When *B. anthracis* vegetative cells are deprived of essential nutrients ("starved"), a trigger is given to begin synthesis of the endospore ("spore"). The following sequence of events takes place when the vegetative cells are starved: 1) an asymmetric septation of starved vegetative cells occurs, resulting in the formation of the mother cell and a forespore; 2) the mother cell engulfs the forespore, thus surrounding the forespore with two opposing cell membranes; 3) a thick layer of modified peptidoglycan ("cortex") is synthesized between the two membranes; and 4) proteins synthesized in the mother cell form multiple layers of a spore coat that covers the cortex.

The spore coat forms the outermost layer for spores of some *Bacillus* species, such as *B. subtilis*. However, in other species, such as *B. anthracis*, the spore is enclosed by an additional layer called the exosporium, a loose balloon-like layer containing proteins, lipid, and carbohydrate. Charlton et al. ("Characterization of the exosporium of *Bacillus cereus*" *J. App. Microbiol.* 87:241-245, 1999) describe studies on the exosporium of *B. cereus*. Spores of the closely related species *B. thuringiensis* also have an exosporium. A number of investigators have previously identified spore coat and exosporium antigens of *B. anthracis*. Lai et al. ("Proteomic analysis of the spore coats of *Bacillus subtilis* and *Bacillus anthracis*" *J. Bact.*, 185(4):1443-1454, 2003), using proteomic analysis employing a combination of SDS-PAGE separation and 2-D electrophoretic separations, followed by matrix-assisted laser desorption ionization-time of flight (MALDI-TOF®), identified 38 spore proteins of *B. subtilis* (of which 12 are known spore coat proteins) and 11 spore proteins of *B. anthracis* (6 of which they identified as candidate coat or exosporium proteins). From their studies comparing *B. subtilis* and *B. anthracis* spore proteins, Lai et al. concluded that "*B. subtilis* and *B. anthracis* coats have roughly similar numbers of proteins and that a core group of coat protein species is shared between these organisms, including the major morphogenetic proteins. Nonetheless, a significant number of coat proteins are probably unique to each species" (underlining added; see Lai et al. abstract)

Steichen et al. ("Identification of the immunodominant protein and other proteins of the *Bacillus anthracis* exosporium", *J. Bact.*, 185(6):1903-1910, 2003) identified five major proteins in purified *B. anthracis* exosporium, including the collagen-like-glycoprotein BclA, which they described as a structural component of the exosporium hair-like nap. These investigators concluded that BclA is the immunodominant antigen on the *B. anthracis* spore surface because 12 out of 20 monoclonal antibodies raised against either spores or purified exosporium reacted with BclA. The other four proteins identified by Steichen et al. are alanine racemase, superoxide dismutase, and two proteins with no significant similarity to any other protein, which they called BxpA and BxpB.

In addition, Todd et al. ("Genes of *Bacillus cereus* and *Bacillus anthracis* encoding proteins of the exosporium", *J. Bact.*, 185(11):3373-3378, 2003) evaluated exosporium proteins of *B. cereus*. *B. cereus* is a member of the *Bacillus cereus* family, which includes *B. thuringiensis* and *B. anthracis*, all of which possess an exosporium and all of which are close relatives. Other related *Bacillus* species include *B. subtilis*, *B. globigii*, *B. pumilis*, *B. mycoides*, and *B. megaterium*. Todd et al. identified 10 exosporium proteins of *B. cereus*. They concluded, based on a comparative analysis of *B. cereus* protein sequences with predicted protein sequences from the *B. anthracis* genome sequences that "from the available unfinished genome sequences, most of the novel Exs proteins are closely conserved between *B. cereus* and *B. anthracis*, with two exceptions . . . a local region of ExsB and the entire ExsC protein that may not be expressed in *B. anthracis*." (see page 3378, first full paragraph). They further note that their "identified genes do not by any means represent an exhaustive list of protein components of the exosporium; one-third of protein remained in the insoluble fraction, and 7 out of 17 bands have not yielded clear N-terminal sequence data." (see page 3378, fourth full paragraph).

In the literature concerning spore coat or exosporium proteins of *B. anthracis*, the only monoclonal antibodies developed were to the immunodominant *Bacillus* collagen-like protein of *anthracis*, BclA (see Sylvestre et al., "A collagen-like surface glycoprotein is a structural component of the *Bacillus anthracis* exosporium" *Molec. Microbiol.* 45(1):169-178, 2002; and Steichen et al.). Longchamp et al. ("Molecular recognition specificity of *Bacillus anthracis* spore antibodies" *J. App. Microbiol.* 87:246-249, 1999) describe the characterization of polyclonal serum which recognized a wide range of spore surface epitopes which cross-reacted with related *Bacillus* species. They further describe two monoclonal antibodies that did not react with spore surface epitopes. Lee et al. (WO 01/49823) describe antibodies against a *B. anthracis* surface array protein, to which the 23a-14G9 monoclonal antibody of the instant invention as described below does not react.

Citation of documents herein is not intended as an admission that any is pertinent prior art. All statements as to the date or representation as to the contents of documents is based on the information available to the applicant and does not constitute any admission as to the correctness of the dates or contents of the documents.

BRIEF SUMMARY OF THE INVENTION

The invention relates to an antigen found on spores of *Bacillus* species and strains relative to the vegetative or actively growing forms. The antigen is present and detectable on ungerminated spores. Detection of the antigen, or fragments thereof, may be advantageously used in a method, procedure, assay or test to rapidly detect and identify *Bacillus* spores, including *B. anthracis* spores, in an accurate and specific fashion. The antigen, as well as fragments thereof, also may be used to generate antibodies that are specific for spores and so capable of detecting a spore relative to a vegetative cell or other actively growing form of *Bacillus*.

The antigen contains epitopes that are the same in multiple *Bacillus* species and strains. Thus *Bacillus* spores of many species or strains may be identified by some epitopes of the antigen. Identification may be based on the antigenicity of the epitopes or by the underlying amino acid or nucleic acid sequence of the epitopes. Other epitopes of the antigen are limited to pathogenic and/or toxigenic *Bacilli*. These latter epitopes may be advantageously used to identify spores of pathogenic and/or toxigenic *Bacilli*. Epitopes that may be used to detect spores of particular pathogenic *Bacilli* are also provided.

The antigen is a glycosyl hydrolase (GH) present and detectable on *Bacillus* spores. The antigen has been referred to as a member of family 18 in a classification of glycosyl hydrolases based on amino acid sequence similarities. The sequences of various *Bacillus* glycosyl hydrolases are available, including that of glycosyl hydrolase from various strains of *B. anthracis*. Accessible sequences are referenced as follows: GI 65320886 (ZP_00393845.1); GI 47528953 (YP_020302.1); GI 49186406 (YP_029658.1); GI 47504101 (AAT32777.1); GI 49180333 (GB AAT55709.1); GI 30263554 (NP_845931.1); and GI 30258189 (GB AAP27417.1). These represent sequences of various *B. anthracis* strains, including the Ames Ancestor, the Sterne strain, the Ames strain, and the A2012 strain. The instant invention is believed to be based in part on the discovery that expression of these GH sequences is detectable as an antigen on ungerminated *Bacillus* spores.

The present invention provides for the detection and use of *Bacillus* GH polypeptides. In some embodiments, the invention provides for the use of the full length polypeptide, represented herein by SEQ ID NO:1 and otherwise identified by accession number ZP_00393845 (originating from *Bacillus anthracis* strain A2012), as well as fragments thereof. The invention includes the use of immunogenic fragments, such as those which contain an epitope of *Bacillus* GH.

SEQ ID NO:1 represents a polypeptide of 430 amino acids in length. The polypeptide was observed in a non-denaturing immunoblot to have a relative molecular weight of about 43-45 kD. This antigen, or fragments thereof, may be used to generate antibodies which bind it, as well as fragments thereof, via the cognate epitope(s) recognized by the antibodies. The detection of this antigen, or fragments thereof, may be used to detect the presence of the antigen and so spore(s) of *Bacillus*.

In another aspect, the invention provides epitopes of the antigen which may be advantageously used in the practice of the invention. In one embodiment, the epitope contains the sequence is ISSVAAVALA, which corresponds to positions 342-351 of SEQ ID NO:1. In other embodiments, the invention provides for polypeptides containing this epitope optionally in combination with other epitopes, or other amino acid sequences (or domains), of the antigen. Such polypeptides may be used to generate antibodies which recognize and bind the antigen or fragments thereof. Such antibodies may be used to detect the antigen and so spore(s) of *Bacillus*. Additional epitopes are provided below.

In a further aspect, the invention provides antibodies which recognize and bind the *Bacillus* GH antigen. The antibodies may be used to detect GH as present on *Bacillus* spores and so may be used to detect the presence or absence of *Bacillus* spores. Antibodies against particular GH epitopes may be used to detect particular *Bacillus* spores that display that epitope. In some embodiments, the antibodies may be used to detect the spores of pathogenic and/or toxigenic *Bacilli*. Thus the invention provides for the formation and detection of a complex of a GH binding antibody and its cognate GH epitope, such as that present on a *Bacillus* spore.

The antibodies of the invention may be monoclonal or polyclonal. In some embodiments, the invention relates to a murine monoclonal antibody identified as 23a-14G9, which binds to a *B. anthracis* GH polypeptide. The antibody is specific for the spores of *B. anthracis* relative to the vegetative form of the cells.

The invention also provides alternative forms of GH binding monoclonal antibodies. These include, but are not limited to, binding fragments of the antibody as well as hybrid, chimeric, altered, recombinant, or humanized forms of the antibody which bind *Bacillus* GH polypeptides and *Bacillus* spores. Non-limiting examples of antibody fragments include bivalent F(ab')$_2$ fragments, such as those produced by digestion with pepsin, and monovalent Fab fragments, such as those produced by digestion with papain.

In another aspect, the invention provides additional monoclonal and polyclonal antibodies that bind the spore specific GH antigen. These additional antibodies may be produced by routine methods known in the field, such as inoculation with a GH polypeptide or spore preparation containing immunogenic portions of the GH polypeptide. Such preparations include simply spores that "display" or otherwise present or expose an immunogenic GH epitope.

The resulting antibodies may be used to generate hybridoma cells that express each antibody as a monoclonal. The hybridomas may then be screened or otherwise selected to identify those that express a monoclonal antibody that binds/recognizes particular epitopes of the spore specific GH antigen. Such epitopes may be the same or different than that recognized by the 23a-14G9 antibody. Antibodies that are specific for *Bacillus* spores may be used or applied as described herein.

In a further aspect, a composition comprising an antibody of the invention, or alternative form thereof, is provided. The compositions include articles of manufacture, as well as kits, comprising one or more of the antibodies and alternative forms thereof. The compositions may further comprise one or more other reagent for the detection of *Bacillus*, such as *B. anthracis, B. thuringiensis, B. cereus,* or other *Bacillus* species. Non-limiting examples of articles of manufacture include test devices like plates, dishes, and wells for the detection of *Bacillus*. Kits of the invention include those comprising other reagents used in the detection of *Bacillus*. Non-limiting examples include those suitable for use with the detection methods described herein.

Other compositions of the invention include those comprising a GH polypeptide or fragment thereof. In some embodiments, the composition is immunogenic and so may be used to generate GH antibodies or serve as a reagent for binding to a GH reactive antibody. Non-limiting examples of a GH reagent include a polypeptide used as a positive control for a GH reactive antibody.

In yet another aspect, the invention provides for methods to detect the presence of *Bacillus* spores by detection of the GH antigen. In some embodiments, the detection may be by use of the antibodies and alternative forms thereof as disclosed herein. The methods of the invention are not, however, limited by format or design. The methods may be conducted qualitatively or quantitatively to detect *Bacillus* spores. The methods may also be used to detect pathogenic and/or toxigenic *Bacilli*.

In some embodiments, a method to detect the presence or absence of *B. anthracis* spores in a sample, such as a medical sample of material obtained from a subject, including from the skin or clothing of the subject, is provided. Alternatively, the sample may be an environmental sample, such as a soil or air sample, or a sample of material suspected of containing spores, such as suspicious powders. The method comprises detecting the presence of a GH antigen, such as by binding to an antibody of the invention, as a component present in the sample. This may comprise the formation of a bound complex comprising the GH antigen, in the sample, and the antibody.

The invention further provides a hybridoma cell that produces the 23a-14G9 antibody. The cell was deposited with the ATCC on May 19, 2004 and identified by ATCC accession number PTA-6004. The hybridoma may be cultured in vitro to produce antibodies for use as disclosed herein, after an optional purification or isolation step. Alternatively, the hybridoma may be introduced into an animal to form an ascites from which antibody containing fluid may be obtained. The resultant antibodies may be used as disclosed herein, after an optional purification or isolation step.

BRIEF DESCRIPTION OF THE DRAWINGS

FIG. 1 shows an alignment of antigen sequences from various *Bacillus* species, including *B. anthracis*, (SEQ ID NO:1) *B. thuringiensis* (Bt) (SEQ ID NOS:2 and 8), and *B. cereus* (Bc) (SEQ ID NOS:3-7).

FIG. 2 shows the specificity of 23a-14G9 for *B. anthracis* spores relative to vegetative cells in a capture ELISA assay.

FIG. 3 shows the specificity of 23a-14G9 for *B. anthracis* spores relative to other *Bacillus* spores.

FIG. 4 shows that 23a-14G9 has partial cross reactivity with spores of one isolate of *B. thuringiensis* (subsp. *Kurstaki* ATCC 33679). Generally, use of 23a-14G9 to detect *B. anthracis* produces a signal that is at least about double that of the *Kurstaki* isolate.

FIG. 5 shows that 23a-14G9 has reactivity with spores of *B. cereus* ZK.

DETAILED DESCRIPTION OF MODES OF PRACTICING THE INVENTION

The invention is based in part on an antigen found on spores of *Bacillus* species and strains relative to the vegetative or actively growing forms. The antigen is present and detectable on ungerminated spores, which is advantageous in applications where spore detection is desired. Ungerminated spores are readily identified based upon a refractive appearance under phase contrast microscopy, while germinated spores are not refractive. Sequences of the antigen from various *Bacilli* are provided. The antigen varies between different *Bacilli* such that certain epitopes may be use to detect certain *Bacillus* spores contain the epitopes. In some embodiments, the invention provides for the detection of an epitope common to pathogenic and/or toxigenic *Bacilli*.

The antigen also contains regions that are conserved. Such regions may be used as epitopes common to *Bacillus* spores. Common epitopes may be used in various ways, including a means to "capture" or immobilize *Bacillus* spores to facilitate the detection of another epitope, such as an epitope found on spores of a particular species or strain or of pathogenic and/or toxigenic *Bacilli*.

The antigen is a *Bacillus* glycosyl hydrolase (GH). The invention is based in part on its presence and detectability on *Bacillus* spores. In some embodiments, the antigen is represented by SEQ ID NO:1 which is aligned with other sequences in FIG. 1 to show the extent of variation among different *Bacilli*.

The invention also provides for the preparation and use of *Bacillus* GH polypeptides. These include polypeptides of an entire *Bacillus* GH as well as fragments thereof, where fragments are less than full length polypeptides with a contiguous portion (or contiguous sequence) of a *Bacillus* GH. Larger polypeptides containing such fragments may also be used. In some embodiments, the polypeptides comprise the sequence of an epitope of GH that is specific to *Bacillus* spores.

The invention includes isolated polypeptides of a *Bacillus* GH. Non-limiting examples include a polypeptide with the sequence of SEQ ID NO:1 or polypeptides with the sequence of a fragment of SEQ ID NO:1. The fragments may be of any length below 430 amino acids, but should be of 10 amino acid residues or longer. Non-limiting embodiments of polypeptides include polypeptides with lengths of 11, 12, 13, 14, 15, 16, 17, 18, 19, 20, about 22, about 24, about 26, about 28, about 30, about 33, about 36, about 39, about 42, about 45, about 48, about 50, about 55, about 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 270, about 290, about 310, about 330, about 350, about 370, about 390, about 410 amino acid residues. In some embodiments, a polypeptide from 10 to 233 (or thereabout) amino acid residues, such as length of 162 (or thereabout) residues is used, optionally containing glutamic acid at position 207. As noted above, larger polypeptides containing such fragments may also be used in the practice of the invention.

In other embodiments, the polypeptides may be categorized by actual or relative molecular weight, such as about 1 kD, about 1.5 kD, about 2 kD, about 2.5 kD, about 3 kD, about 3.5 kD, about 4 kD, about 4.5 kD, about 5 kD, about 5.5 kD, about 6 kD, about 6.5 kD, about 7 kD, about 7.5 kD, about 8 kD, about 8.5 kD, about 9 kD, about 9.5 kD, about 10 kD, about 12 kD, about 14 kD, about 16 kD, about 18 kD, about 20 kD, about 22 kD, about 24 kD, about 26 kD, about 28 kD, about 30 kD, about 35 kD, or about 40 kD may be used. As would be recognized by the skilled artisan, actual molecular weight may be based upon the exact sequence of a polypeptide while relative molecular weight may be determined by means such as gel electrophoresis.

The polypeptides of the invention may be produced by a variety of means known to the skilled person. These include isolation from naturally occurring sources as well as synthetic preparation, such as de novo peptide synthesis. A polypeptides is "isolated" when it is separated from one or more components normally found with the polypeptide or when the composition containing the polypeptide predominantly contains the polypeptide such that they are present, on a molar basis, more abundantly than other polypeptide entities in the composition. But in the case of de novo produced polypeptides, they need not be "isolated" before certain uses described herein, such as when used to generate antibodies that bind them.

In many embodiments, a polypeptide of the invention includes the sequence of a particular GH epitope. In some embodiments, the epitope sequence is ISSVAAVALA, which corresponds to positions 342-351 of SEQ ID NO:1. Other epitope sequences include AISSVAAVALA, which corresponds to positions 341-351 of SEQ ID NO:1; ISSVAAVALAR, which corresponds to positions 342-352 of SEQ ID NO:1; AISSVAAVALAR, which corresponds to positions 341-352 of SEQ ID NO:1; KAISSVAAVALA, which corresponds to positions 340-351 of SEQ ID NO:1; KAISSVAAVALAR, which corresponds to positions 340-352 of SEQ ID NO:1; AKAISSVAAVALAR, which corresponds to positions 339-352 of SEQ ID NO:1; PAKAISSVAAVALAR, which corresponds to positions 338-352 of SEQ ID NO:1; PPAKAISSVAAVALAR, which corresponds to positions 337-352 of SEQ ID NO:1; NPPAKAISSVAAVALAR, which corresponds to positions 336-352 of SEQ ID NO:1; GNPPAKAISSVAAVALAR, which corresponds to positions 335-352 of SEQ ID NO:1; KAISSVAAVALARK, which corresponds to positions 340-353 of SEQ ID NO:1; KAISSVAAVALARKY, which corresponds to positions 340-354 of SEQ ID NO:1; KAISSVAAVALARKYN, which corresponds to positions 340-355 of SEQ ID NO:1; KAISSVAAVALARKYNV, which corresponds to positions 340-356 of SEQ ID NO:1; KAISSVAAVALARKYNVP, which corresponds to positions 340-357 of SEQ ID NO:1; EGNPPAKAISSVAAVALA, which corresponds to positions 334-351 of SEQ ID NO:1; EGNPPAKAISSVAAVALAR, which corresponds to positions 334-352 of SEQ ID NO:1; EGNPPAKAISSVAAVALARK, which corresponds to positions 334-353 of SEQ ID NO:1; EGNPPAKAISSVAAVALARKY, which corresponds to positions 334-354 of SEQ ID NO:1; EGNPPAKAISSVAAVALARKYN, which corresponds to positions 334-355 of SEQ ID NO:1; EGNPPAKAISSVAAVALARKYNV, which corresponds to positions 334-356 of SEQ ID NO:1; and EGNPPAKAISSVAAVALARKYNVP, which corresponds to positions 334-357 of SEQ ID NO:1. Of course larger fragments that contain these epitope sequences may also be prepared and used. Such larger fragments may be those of Bacillus GH as described above. In some embodiments, the larger fragment may have one of the above epitopes at or near the N-terminus and then have all or part of the remainder of the Bacillus GH (up to position 430 of SEQ ID NO:1) to the C-terminal side of the epitope.

Another epitope sequence is YIPKGTKRAV, which corresponds to positions 95-104 of SEQ ID NO:1. Other epitope sequences include LYIPKGTKRAV, which corresponds to positions 94-104 of SEQ ID NO:1; QLYIPKGTKRAV, which corresponds to positions 93-104 of SEQ ID NO:1; QQLYIPKGTKRAV, which corresponds to positions 92-104 of SEQ ID NO:1; GQQLYIPKGTKRAV, which corresponds to positions 91-104 of SEQ ID NO:1; YIPKGTKRAVE, which corresponds to positions 95-105 of SEQ ID NO:1; YIPKGTKRAVES, which corresponds to positions 95-106 of SEQ ID NO:1; YIPKGTKRAVESI, which corresponds to positions 95-107 of SEQ ID NO:1; YIPKGTKRAVESIA, which corresponds to positions 95-108 of SEQ ID NO:1; YIPKGTKRAVESIAY, which corresponds to positions 95-109 of SEQ ID NO:1; YIPKGTKRAVESIAYL, which corresponds to positions 95-110 of SEQ ID NO:1; YIPKGTKRAVESIAYLQ, which corresponds to positions 95-111 of SEQ ID NO:1; YIPKGTKRAVESIAYLQP, which corresponds to positions 95-112 of SEQ ID NO:1; LYIPKGTKRAVE, which corresponds to positions 94-105 of SEQ ID NO:1; QLYIPKGTKRAVES, which corresponds to positions 93-106 of SEQ ID NO:1; QQLYIPKGTKRAVESI, which corresponds to positions 92-107 of SEQ ID NO:1; GQQLLYIPKGTKRAVESIA, which corresponds to positions 91-108 of SEQ ID NO:1; GQQLLYIPKGTKRAVESIAY, which corresponds to positions 91-109 of SEQ ID NO:1; GQQLLYIPKGTKRAVESIAYL, which corresponds to positions 91-110 of SEQ ID NO:1; GQQLLYIPKGTKRAVESIAYLQ, which corresponds to positions 91-111 of SEQ ID NO:1; and GQQLLYIPKGTKRAVESIAYLQP, which corresponds to positions 91-112 of SEQ ID NO:1. Again, larger fragments that contain these epitope sequences may also be prepared and used. Such larger fragments may be those of Bacillus GH as described above. In some embodiments, the larger fragment may have one of the above epitopes at or near the C-terminus and then have all or part of the remaining N-terminal region of the Bacillus GH (up to position 1 of SEQ ID NO:1) to the N-terminal side of the epitope.

In other embodiments, a composition comprising a polypeptide of the invention is provided. A polypeptide or a composition comprising it may be used to generate antibodies against the polypeptide. As a non-limiting example, a polypeptide containing the KAISSVAAVALAR (positions 340-352 of SEQ ID NO:1) epitope sequence, or a composition comprising the polypeptide, may be used to generate antibodies which bind the epitope. In alternative embodiments, a polypeptide or composition comprising it may be used as a ligand or antigen, such as a positive control as a non-limiting example, for use with a receptor, antibody, or other agent which binds the polypeptide. Using the KAISSVAAVALAR (positions 340-352 of SEQ ID NO:1) epitope sequence again as a non-limiting example, a polypeptide comprising this epitope may be used as a ligand, such as a positive control, in combination with an antibody that binds it. One exemplification of such an embodiment is an assay using an antibody that binds this epitope to detect Bacillus spores. A polypeptide containing the epitope may be used as a positive control in the assay to verify that the antibody functioned properly.

The invention also provides for antibodies that bind and recognize the Bacillus spore specific GH antigen. The antibodies may be polyclonal or monoclonal. They may recognize many or a few different species, strains, or isolates of Bacillus. In some embodiments, antibodies that recognize B. anthracis spores, as specific as possible relative to other Bacillus spores, are used to detect B. anthracis with greater specificity. In other embodiments, the antibodies are able to bind spores of B. anthracis as well as other Bacilli such that the antibodies may be used to immobilize Bacillus spores for further testing or study. In additional embodiments, the antibody may be an isolated antibody which binds glycosyl hydrolase on ungerminated Bacillus spores. The Bacillus spores may be of a pathogenic and/or toxigenic Bacilli, such as B. anthracis. As known to the skilled person, pathogenic and/or toxigenic Bacilli include those classified as B. thuringiensis or B. cereus.

The invention further provides an antibody which binds a GH antigen with the sequence of SEQ ID NO:1. Such an antibody may bind a GH epitope comprising ISSVAAVALA (positions 342-351 of SEQ ID NO:1).

The invention also provides for a complex comprising a GH binding antibody and a *Bacillus* spore. The complex may be optionally isolated, or immobilized, such as where the GH binding antibody is immobilized on a solid support.

In some embodiments, the invention provides a murine monoclonal antibody identified as 23a-14G9, which is specific for *Bacillus* spores relative to the vegetative form of the cells. The antibody, as well as GH antigen binding forms thereof, may thus be used to differentially detect spores from vegetative cells. The antibody is also specific for spores of some pathogenic *Bacilli* relative to spores of other *Bacilli*. Thus the invention also provides for the use of the antibody, as well as spore binding alternative forms thereof, to differentially detect spores of pathogenic *Bacilli* from other *Bacillus* spores.

Without being bound by theory, and offered to improve the understanding of the invention, the 23a-14G9 antibody is believed to bind the KAISSVAAVALAR (positions 340-352 of SEQ ID NO:1) epitope, which in turn is believed to be specific for certain pathogenic *Bacilli*, including *B. anthracis*, *B. thuringiensis* 97-27, and *B. cereus* ZK (or E33L). These pathogenic *Bacilli* have been classified as part of "Branch F" in an extensive classification of 310 *B. anthracis*, *B. thuringiensis*, and *B. cereus* isolates (see Hill et al. "Fluorescent amplified fragment length polymorphism analysis of *B. anthracis*, *B. cereus*, and *B. thuringiensis* isolates." *App. Envir. Micro.* 70(2):1068-1080, 2004). The analysis included 24 geographically diverse *B. anthracis* isolates. All *B. anthracis* isolates as well as pathogenic and toxigenic *B. thuringiensis* (including 97-27) and *B. cereus* isolates are present in "Branch F". The *B. anthracis* isolates mapped to one location within the Branch. Thus the antibody, as well as the KAISSVAAVALAR (positions 340-352 of SEQ ID NO:1) epitope is believed to be specific to pathogenic and/or toxigenic *Bacilli*.

The 23a-14G9 antibody was tested against spores of 12 virulent *B. anthracis* isolates from geographically diverse regions of the world (USA, Canada, China, Germany, South Africa, United Kingdom, Brazil, Turkey, Australia, and Namibia). The isolates were from both human and animal sources and are listed in Table 1 below. All virulent spore preparations tested strongly positive with 23a-14G9 as the detector antibody and rabbit polyclonal anti-*B. anthracis* IgG as the capture antibody.

TABLE 1

| Isolate # | Original ID | Origin | Source |
| --- | --- | --- | --- |
| A0308 | 91-382C-1 | Canada (AB) | Bovine |
| A0033 | 23/32 | China | Wool |
| A0286 | 22 | Turkey (Sivas) | Human |
| A0328 | A30 | Germany (Hessen) | Pig |
| A0446 | 11749 | Namibia (Etosha NP) | Elephant |
| A0462 | 11963 | CAMR/Porton UK | Not reported |
| A0220 | 97-1946/2 | Australia (Victoria) | Bovine blood |
| A0435 | K3 | South Africa (Kruger NP) | Kudu |
| A0248 | #28 | USA (OH) | Human |
| A0488 | Vollum | UK VOLLUM | Not reported |
| A0442 | K88 | South Africa (Kruger NP) | Kudu |
| A0067 | Asc 65 | Brazil | Milk |

The antibodies of the invention may be referred to as being "specific for" or "specifically immunoreactive with" *Bacillus* spores. These terms refer to the ability of the antibody to react in a binding reaction to *Bacillus* spores, or the cognate antigen found in these spores. The reaction can be determinative of the presence or amount of *Bacillus* spores in the presence of other proteins, spores, or cells. Under assay conditions as desired by the skilled practitioner, including the non-limiting conditions disclosed herein, the antibody binds preferentially to *Bacillus* spores, or the cognate antigen found therein, and does not bind in a significant or detectable manner to other factors in a sample. Preferred embodiments of the invention utilize conditions wherein the antibody, or an alternative form thereof, selectively binds to produce a signal which is at least twice, preferably at least 10 times to 100 times, background signal or noise. Background signal or noise may include low level cross reactivity with other spores. In the case of an antibody like 23a-14G9, the low level cross reactivity may be with spores such as those of *B. thuringiensis* subsp. *Kurstaki* 33679.

In additional embodiments, the invention provides antibodies that recognize or bind an epitope specific to the spore specific GH antigen of *Bacilli*. In some cases, this may be the epitope bound by the 23a-14G9 antibody. For some antibodies, the binding may be specific for the antigen. For other antibodies, the binding may be to an epitope present in a complex of the spore specific GH antigen bound to another antibody, such as the 23a-14G9 antibody.

Alternative forms of the spore specific GH antigen binding antibodies of the invention and the 23a-14G9 monoclonal antibody, which is of the IgG class, can be readily produced by methods known in the art. The ability to produce antigen binding fragments of antibodies is well known and may be utilized to produce bivalent $F(ab')_2$ and monovalent Fab fragments for use as disclosed herein. As used herein, "Fab" refers to double chain binding fragments of antibodies comprising at least functionally complete light and heavy chain variable domains. Additionally, methods for the production of hybrid, chimeric, altered, recombinant (including single chain), or humanized forms of antibodies are also known in the art. These antibody forms may be considered derivatives of a monoclonal antibody disclosed herein.

Additional derivative forms include antibodies of the invention, and alternative forms thereof, that have been conjugated to other chemical moieties. Non-limiting examples include a labeled antibody or an alternative form thereof. The term "label", "detectably labeled" or "labeled with a detectable marker" refer to an antibody composition capable of producing a detectable signal indicative of the presence of the labeled molecule. Suitable labels include radioisotopes, a dye, colloidal gold or a similarly detectable marker, nucleotide chromophores, enzymes, substrates, fluorescent molecules, chemiluminescent moieties, magnetic particles, bioluminescent moieties, and the like, including labels suitable for indirect detection, such as biotin. As such, a label is any composition detectable by spectroscopic, photochemical, biochemical, immunochemical, electrical, optical or chemical means. A label may be attached by use of a chemical linker. Exemplary labels are those that produce a visible signal that can be detected by visual inspection, such as with the unaided human eye.

The antibodies of the invention and alternative forms thereof may also be conjugated by known methods and means to a solid phase support such as, but not limited to, glass, plastic, a synthetic membrane. Other non-limiting examples include beads, particles, dipsticks, fibers, filters, Petri dishes, ELISA (enzyme-linked immunosorbent assay) plates, microtiter plates, silane or silicate supports such as glass slides, and dishes, wells or containers, as well as the sides thereof. Such immobilized forms of the antibodies may be used in the detection methods disclosed herein. They may also be used for immunoaffinity chromatography of *Bacillus* GH polypeptide(s) or spores.

The antibodies of the invention and alternative forms thereof may also be formulated into compositions. The compositions may further comprise one or more other reagent for the detection of *Bacillus*. Non-limiting examples include complexes of the antibody bound to its cognate *Bacillus* spore specific GH antigen and combinations of the antibody with other reagents for use in antibody based detection methods. Other examples include mixtures with other *Bacillus* binding antibodies or detection agents. Combinations of the antibodies, and alternative forms thereof, with other detection agents may also be part of articles of manufacture, such as testing devices, used to detect *Bacillus*.

In some embodiments, the invention provides for an additional reagent to distinguish one type of *Bacillus* spore from another. In some non-limiting cases, the reagent is used in distinguishing *B. anthracis* spores from other pathogenic or toxigenic *Bacillus* spores. As a non-limiting example, an antibody against the KAISSVAAVALAR (positions 340-352 of SEQ ID NO:1) epitope may recognize and detect *B. anthracis* spores as well as spores of *B. thuringiensis* 97-27 and *B. cereus* ZK if present. The additional reagent may be used to distinguish which of these possible spores have been detected.

In some embodiments, an additional reagent is a second antibody that is specific for *B. anthracis* spores, such as an antibody or other binding agent that is specific for the 265Thr containing epitope in SEQ ID NO:1. That threonine residue is not present in the GH sequence of either *B. thuringiensis* 97-27 or *B. cereus* ZK and so may be used to distinguish them from *B. anthracis*. Of course such an antibody or binding agent may also be suitable for detecting *B. anthracis* spores directly, with reduced consideration of cross reactivity with *B. thuringiensis* 97-27 or *B. cereus* ZK spores. Another example of such a reagent is an antibody or other binding agent that recognizes an epitope resulting from a combination of the 265Thr residue with the KAISSVAAVALAR (positions 340-352 of SEQ ID NO:1) epitope. Such a combination would not be present on *B. thuringiensis* 97-27 and *B. cereus* ZK spores.

In other embodiments, an additional reagent is an antibody or other binding agent that is specific for *B. thuringiensis* 97-27 and/or *B. cereus* ZK spores relative to *B. anthracis* spores. Non-limiting examples include antibodies or binding agents that are specific for an epitope resulting from an alanine residue at position 265 in GH. As noted above, *B. anthracis* GH contains a threonine residue at that position and so *B. anthracis* spores would not be reactive with such an antibody or binding agent. Other non-limiting examples include antibodies or other binding agents that are specific for an epitope resulting from a serine residue at position 124 or an asparagine residue at position 242 in GH. These epitopes correspond to sequences present in the GH of *B. cereus* ZK. *B. anthracis* GH contains an alanine at position 124 and a serine at position 242 and so *B. anthracis* spores would not be reactive with such an antibody or binding agent. Thus if a spore containing sample reacts with both an antibody against the KAISSVAAVALAR (positions 340-352 of SEQ ID NO:1) epitope and a *B. cereus* ZK epitope as described above, then the sample contains *B. cereus* ZK spores and only might contain *B. anthracis* spores.

In further embodiments, the additional reagent may be for the detection of nucleic acid sequences that are specific to *B. anthracis* or *B. thuringiensis* 97-27 and/or *B. cereus* ZK. Thus where an antibody against the KAISSVAAVALAR (positions 340-352 of SEQ ID NO:1) epitope detects *Bacillus* spores, the additional reagent may be used to detect one or more nucleic acid sequences that are 1) specific for *B. anthracis*; or 2) specific for *B. thuringiensis* 97-27 and/or *B. cereus* ZK relative to *B. anthracis*. With respect to approach 1, any *B. anthracis* specific sequence may be used, including, as a non-limiting example, a sequence encoding the 265Thr residue in SEQ ID NO:1. In approach 2, the sequence specific for *B. thuringiensis* 97-27 and/or *B. cereus* ZK relative to *B. anthracis* may be any sequence not found in *B. anthracis*, including a sequence that if found in other *Bacillus* species or strains (but not *B. anthracis* isolates). In either approach, all or a distinguishing part of the GH coding sequence may be used as the means to identify the species or strain of *Bacillus*.

Non-limiting examples of such nucleic acid detecting reagents include those for use with nucleic acid detection methods, such as nucleic acid primer and probes for PCR analysis or Southern blotting. In some embodiments, the additional reagent will be suitable for use with quantitative PCR, such that the amount of *B. anthracis* or *B. thuringiensis* 97-27 and/or *B. cereus* ZK nucleic acid material may be determined.

The invention also provides a method of detecting the presence or absence of ungerminated *Bacillus* spores. The method may be used in cases of a sample suspected of containing such spores. In some embodiments, the method may include detecting the binding of an antibody of the invention to such spores. The method may thus include contacting the spores, or a sample containing them, with an antibody as described herein to allow the formation of a complex of antibody bound spores. The complex may then be detected to detect the presence of the spores. As described herein, the spores may be spores of pathogenic and/or toxigenic *Bacilli*, such as *B. anthracis*. In some embodiments, the method is performed with an antibody that binds a GH epitope comprising ISSVAAVALA (positions 342-351 of SEQ ID NO:1).

After determination of the presence of *Bacillus* spores, the method may further comprise identifying said spores as spores of *B. anthracis* or other *Bacilli*. Non-limiting embodiments include identifying the cells to not be spores of *B. thuringiensis* and/or *B. cereus*. Such identification may be by use of an additional reagent as described above to determine the spores as a *B. anthracis* by detection of a *B. thuringiensis* and/or *B. cereus* specific epitope or nucleic acid sequence.

The methods used to detect the presence of *Bacillus* spores are not limited by design. Non-limiting examples include methods utilizing the antibodies of the invention (and optionally the additional reagent(s) described above), and alternative forms thereof as described herein, and based upon the principles of Western blotting or other immunoblotting, ELISA, lateral flow devices, sandwich assays, visual observation by microscopy, competitive and non-competitive immunoassays, immunoenzymetric assays, immunofluorescence, immunomagnetic selection, and flow cytometry (including detection by polychromatic flow cytometry). Additional immunoassay formats are described by Harlow and Lane (1988) *Antibodies, A Laboratory Manual*, Cold Spring Harbor Publications, New York. The methods of the invention are used to qualitatively or quantitatively detect the presence or absence of *Bacillus* spores in a sample or "test sample".

As used herein, a "sample" or "test sample" refers to a sample isolated from an individual infected with, or suspected of being infected with, *B. anthracis* or other pathogenic and/or toxigenic spores as well as environmental samples suspected of containing such spores. Alternatively, the terms refer to samples known to contain such spores for use as a control in the detection methods of the invention or for use in the disclosed detection methods to confirm the presence of, or quantify the amount of, *Bacillus* spores. The sample may be collected by any appropriate means, including sampling of the outer skin or hair, as well as clothing, in cases of a animal or human subject, and sampling of air, paper, soil, or other solid objects in cases of an environmental sample, such as that from a site suspected to contain *B. anthracis* or other pathogenic and/or toxigenic spores. Medical samples also include sampling or swabbing of a subject's bodily surfaces, including, but not limited to, nasal and oral cavities. Other sample forms include samples of water or food. A sample may also be a powder or granulated material suspected of containing *B. anthracis* or other pathogenic and/or toxigenic spores. A sample of the invention may also be an extract of such spores or extract of material containing spores or suspected of containing such spores. In some embodiments of the invention, a sample may be diluted with a sample diluent before being assayed. The diluent may be any suitable solvent as desired by the skilled person.

In cases of air or gas samples, a cyclonic collection device may be used to collect the sample as a non-limiting example. Such a device collects a volume of air or gas and deposits particulates contained therein to a moist surface or liquid medium.

In one embodiment, the invention provides a detection method based on the use of a capture reagent which binds *Bacillus* spores to form a complex therewith. The capture reagent may be the monoclonal antibody, or alternative forms thereof, as described herein. Alternatively, the reagent may be another antibody which binds *Bacillus* spores, including, but not limited to, polyclonal or recombinant antibodies that bind a plurality of *Bacillus* spores and cells. In another embodiment, the capture reagent binds at least the spores of *B. thuringiensis, B. cereus, B. pumilis, B. subtilis*, and *B. megaterium* in addition to *B. anthracis*. The capture reagent may be immobilized on a solid phase support, optionally prior to contact with *Bacillus* spores, as described herein for antibodies of the invention. The reagent need not bind the KAISSVAAVALAR (positions 340-352 of SEQ ID NO:1) epitope or the same epitope as that bound by the 23a-14G9 antibody of the invention. Of course capture agents that bind a complex of the spore (or spore specific antigen) and a spore specific antibody, rather than the antibody alone, may also be used in the practice of the invention.

Whether used with a capture reagent or not, the invention also provides for a detection agent that binds *Bacillus* spores to directly or indirectly indicated their presence or amount. The detection agent is preferably an antibody of the invention, or an alternative form thereof, which binds the spore specific GH antigen. Upon binding, the detection agent forms a bound complex with its binding partner. The detection agent may be detectably labeled such that the presence or amount of the cognate binding partner, and thus *Bacillus* spores, is signaled by the label after binding of the detection agent. Alternatively, the detection agent is itself bound by a detectably labeled secondary agent. As a non-limiting example where the detection agent is 23a-14G9, a detectably labeled anti-murine IgG antibody may be used to detect 23a-14G9 and thus *Bacillus* spores.

When used in combination with a capture reagent, a sandwich complex comprising the reagent, a *Bacillus* spore or spore extract component, and the detection agent is formed. This sandwich complex may be preceded by formation of a complex comprising the capture reagent and a *Bacillus* spore or spore extract component, which complex is exposed to the detection agent to form the sandwich complex. Alternatively, the sandwich complex may be preceded by formation of a complex comprising the detection reagent and a *Bacillus* spore or spore extract component, which complex is subsequently exposed to the capture reagent to form the sandwich complex. The specificity of the sandwich complex, as well as other formats, can be introduced by either the capture reagent, the detection reagent, or both. Thus embodiments of the invention include use of the following combinations:

| Capture reagent | Detector reagent |
| --- | --- |
| Polyclonal antibodies that bind the spore specific GH antigen, optionally binding other antigens | Monoclonal antibody that binds the spore specific GH antigen |
| Polyclonal antibodies that bind a complex comprising the spore specific GH antigen, optionally binding other antigens | Monoclonal antibody that binds the spore specific GH antigen |
| Monoclonal antibody that binds the spore specific GH antigen | Polyclonal antibodies that bind the spore specific GH antigen, optionally binding other antigens |
| Monoclonal antibody that binds the spore specific GH antigen | Polyclonal antibodies that bind a complex comprising the spore specific GH antigen, optionally binding other antigens |
| Monoclonal antibody that binds the spore specific GH antigen | Monoclonal antibody that binds the spore specific GH antigen |

The methods of the invention, with or without the use of a sandwich format, advantageously detect the presence of *Bacillus* spores via the GH antigen at concentrations at least above 0.02 µg/ml. In other embodiments, the methods detect concentrations above 0.08, above 0.30, above 0.5, above 1, or above 1.25 µg/ml. Alternatively, the methods of the invention may be used to detect the presence of *Bacillus* spores at concentrations of at least $10^{10}$, at least $10^9$, at least $10^8$, at least $10^7$, at least $10^6$, or at least $10^5$ cfu/ml by analysis of an aliquot of a sample, or diluent thereof, containing spores at such concentrations. Non-limiting examples of aliquot volumes include 500 µl, 450 µl, 400 µl, 350 µl, 300 µl, 250 µl, 200 µl, or 150 µl sample sizes.

The detection methods of the invention may also include competitive binding assays as embodiments. These comprise the use of a labeled form of *Bacillus* spores or spore extract components that compete for binding to a detection agent and/or capture reagent as described herein and analogous to competitive assay methods known in the art. The methods provided by the present invention may also be automated in whole or in part.

The materials for use in the methods of the present invention are ideally suited for preparation of kits produced in accordance with well known procedures. The invention thus provides kits comprising agents for the detection and/or quantitation of *Bacillus* spores, or extracts or disrupted forms thereof, in a sample as described herein. Such kits optionally comprising the agents and/or reagents with an identifying description or label or instructions relating to the use of the kits, or the suitability of the kits, in the methods of the present invention, is provided. Such a kit may comprise containers, each with one or more of the various agents and/or reagents (optionally in concentrated form) utilized in the methods, including, for example, detection agents and/or pre-immobilized forms of capture reagents. A set of instructions or reagent identifiers will also typically be included. Other exemplary kits contain a device or solid phase supports, such as, but not limited to a lateral flow device, a test strip, beads, a membrane, or coated surfaces of a container, dish or well, for the practice of the invention.

The kits may also optionally include a control sample, such as a known sample of immunoreactive *B. anthracis* or other *Bacillus* spores, or the cognate GH antigen bound by the detection agent and/or capture reagent. A control can be present in known quantities for dilution with the sample diluent used to dilute a sample and used as an external control. or added to an actual sample and used as an internal control, optionally for use to determine the sensitivity of the assay in the context of the sample type being tested. The kits can comprise materials for a single assay or for multiple assays.

The invention further provides a hybridoma cell that produces the 23a-14G9 antibody. The cell was deposited with the ATCC on May 19, 2004 and identified by ATCC accession number PTA-6004. The hybridoma may be cultured in vitro to produce antibodies for use as disclosed herein, after an optional isolation step. Alternatively, the hybridoma may be introduced into an animal to form an ascites from which antibody containing fluid may be obtained. The resultant antibodies may be used as disclosed herein, after an optional isolation step. "Isolation" refers to preparation of a composition that predominantly contains the antibodies such that they are present, on a molar basis, more abundantly than other non-solvent entities in a composition. Preferably, "isolated antibodies" contain at least about 50, at least about 60, at least about 70, at least about 80, or at least about 90 percent on a molar basis antibodies relative to non-solvent entities. Isolation may be conducted by purification of antibodies to near, or essentially, homogeneity by removal of contaminating molecular entities.

Additional monoclonal antibodies can be produced in the manner used to produce 23a-14G9. Briefly, mice were exposed to *B. anthracis* spores to generate an immune response and the production of antibodies. Antibody expressing cells were isolated and fused to selectable immortalized cells followed by screening for cells expressing antibodies specific for *B. anthracis* spores. Populations of positive cells were cloned by limiting dilution and further selected to obtain the hybridoma cell line that produces 23a-14G9. Other *Bacillus* spores that expose GH on their surface may also be used in an analogous manner.

Antibodies also may be produced by use of a GH polypeptide as described herein. Methods to produce antibodies with a polypeptide as the antigen are well known to the skilled person, and may optionally be performed by commercial service providers. The polypeptides of the invention may be used alone as the antigen or in combination with an agent to enhance antibody production, such as an immunoadjuvant. The invention includes a method of producing an antibody which binds ungerminated *Bacillus* spores by use of a GH polypeptide as antigen. The method may be practiced by inoculating an antibody producing animal with a GH polypeptide of the invention in sufficient quantity to produce antibodies against the polypeptide. Any suitable animal known to the skilled person may be used. Non-limiting examples include a mouse, rat, hamster or other rodent; a goat or other herbivore; and a rabbit.

The GH polypeptide used to prepare antibodies may include an epitope or other immunogenic portion of GH as described herein. In some embodiments, the epitope or immunogenic portion is specific to pathogenic and/or toxigenic *Bacilli* such that the resulting antibodies may be advantageously used to detect the spores of those *Bacilli*. After production of the antibodies in the animal, the antibodies may be obtained as polyclonal serum from the animal or be otherwise isolated, such as by fractionation based on antibody subclasses. Of course the inoculated animals may also be used as a source of cells to generate hybridomas that may be screened to produce monoclonal antibodies as well known to the skilled person.

In some embodiments, the polypeptide used as the antigen has an epitope comprising ISSVAAVALA (positions 342-351 of SEQ ID NO:1) as described herein. Larger polypeptides comprising this epitope may also be used. The larger polypeptide may be the entire GH polypeptide, denatured or in native form, or a fragment thereof. In the case of a native form, the antigen may be a *Bacillus* glycosyl hydrolase as present on *Bacillus* spores.

The resultant antibodies and/or hybridomas may be screened against any *Bacillus* strains or spores or other molecules to which cross reactivity is detected. This allows for the selection of antibodies which would be specific, or more specific, for *B. anthracis* relative to the other to the cross reacting strain or other molecule. In some embodiments of the invention, antibodies or hybridomas are selected relative to spores of *B. thuringiensis* subsp. *Kurstaki*, such as ATCC 33679, which has low level cross reactivity with the 23a-14G9 antibody. Selection relative to ATCC 35866 may also be performed.

Having now generally described the invention, the same will be more readily understood through reference to the following examples which are provided by way of illustration, and are not intended to be limiting of the present invention, unless specified.

EXAMPLES

Example 1

23a-14G9 Recognizes a Spore-Specific Antigen

Materials and Methods
(1) Antigen Preparation
Spores:
*B. anthracis* was grown in confluent cultures on TSA plates for 3 days to allow sufficient time for vegetative cells to deplete essential nutrients from the medium resulting in spore formation. Bacteria/spores were washed off plates in sterile phosphate buffered saline (PBS) and incubated at 60° C. in a water bath for 1 hour to kill remaining vegetative cells while spores remain unaffected. Spores were then washed two times by centrifugation at 3400 rpm for 10 minutes at 4° C. An aliquot of the preparation was stained with malachite green to visualize spores to verify that the preparation contained a preponderance of spores, with very few vegetative cells present.

Vegetative Cell Antigens:
*B. anthracis* vegetative cells were cultured overnight in an aerated liquid culture. Vegetative cells were pelleted by centrifugation, washed, and then lyzed in a TRIS-EDTA buffer solution containing high salt and detergent. The supernatant was dialyzed against PBS.

(2) Capture ELISA

For the capture ELISA, protein G-purified rabbit polyclonal IgG from rabbits immunized with B. anthracis spores and vegetative cells was used as capture antibody and coated unto ELISA plates at a concentration of 10 µg/ml. The ELISA plates were blocked with a blocking solution containing 5% skim milk according to standard procedures. Two fold-serial dilutions of either spore or vegetative cell antigens were incubated in the ELISA plate for 1 hour. The plates were extensively washed, followed by addition of monoclonal antibody (mAb) 23a-14G9 at 10 µg/ml, and incubation for 1 hour. Plates were extensively washed. Development of the ELISA reaction was initiated with goat anti-mouse IgG antibody conjugated with horse radish peroxidase, followed by addition of the substrate ABTS. Plates were read in an ELISA plate reader at an OD of 405 nm.

Results

Results are presented in FIG. 1, which clearly demonstrates that 23a-14G9 reacts strongly with B. anthracis spore antigens but does not react at all with antigens present in vegetative cells of B. anthracis. Thus, 23a-14G9 is a monoclonal antibody which recognizes a spore-specific antigen of B. anthracis.

Example 2

Specificity of 23a-14G9

The relative specificity of B. anthracis spore-specific monoclonal antibody 23a-14G9 is illustrated as follows. A capture ELISA was performed utilizing rabbit polyclonal IgG as the capture antibody and the B. anthracis spore-specific monoclonal antibody 23a-14G9 as the detector antibody. Spores from the following Bacillus organisms were used as antigens: B. anthracis Sterne; B. thuringiensis ATCC 35646; B. cereus ATCC 33018; B. pumilis ATCC 72; B. subtilis ATCC 6051; and B. megaterium ATCC 25833.

As shown in FIG. 2, monoclonal antibody 23a-14G9 reacted only with spores of B. anthracis. The antibody did not react with spores of B. thuringiensis, B. cereus, B. megaterium, B. pumilis, or B. subtilis. Thus, monoclonal antibody 23a-14G9 is relatively specific to B. anthracis and can be used to detect and differentiate B. anthracis spores from these other Bacillus spores.

Using the same conditions, the 23a-14G9 antibody was tested against spores of the following Bacillus isolates: B. cereus ATCC 9620, B. cereus ATCC 14579 (type strain), B. cereus ATCC 49064, B. cereus ATCC 10702, B. cereus ATCC 7004, B. cereus ATCC 33019, B. thuringiensis ATCC 19267, B. thuringiensis ATCC 10792, B. thuringiensis subsp. Israelensis ATCC 39152, B. thuringiensis subsp. Kurstaki ATCC 33679, and B. thuringiensis subsp. Kurstaki ATCC 35866. The antibody was negative against all of these B. cereus isolates and B. thuringiensis isolates, except ATCC 33679 which was partially cross-reactive (see FIG. 3). ATCC 33679 was positive above an antigen concentration of 2.5 µg/ml vs. 0.04 µg/ml for B. anthracis.

Example 3

Reactivity with Pathogenic Bacilli

A direct ELISA was performed with the 23a-14G9 antibody and various antigens as shown in Table 2. Various antibody concentrations were used, and spores of B. anthracis Sterne, B. cereus ZK, B. cereus FRI 42, B. cereus ATCC 7004, B. thuringiensis HD571, B. subtilis ATCC 6051, and B. cereus ATCC 10978 as well as vegetative cells of B. anthracis Sterne were tested. The results are shown in Table 2 and graphically in FIG. 5. Reactivity was only seen with spores of B. anthracis Sterne and B. cereus ZK. Similar results were observed with B. thuringiensis 97-27.

TABLE 2

Direct ELISA: Spore Group 1
Positive
Antibody 14G9 lot T140604-01 at 20 ug/mL
Antigen See Below
Conjugate Goat α Mouse

| Antibody Conc. | B. anthracis Sterne Spore | B. anthracis Sterne Veg | B. cereus ZK | B. cereus FRI 42 | B cereus ATCC 7004 | Antigen Bt. HD571 | B. subtilis ATCC 6051 | B. cereus ATCC 10978 |
|---|---|---|---|---|---|---|---|---|
| 20 ug/mL | 2.068 | 0.092 | 0.992 | 0.184 | 0.108 | 0.108 | 0.071 | 0.095 |
| 10 ug/mL | 2.131 | 0.071 | 0.979 | 0.168 | 0.087 | 0.088 | 0.061 | 0.081 |
| 5 ug/mL | 2.146 | 0.064 | 0.979 | 0.147 | 0.076 | 0.091 | 0.061 | 0.074 |
| 2.5 ug/mL | 2.126 | 0.060 | 0.902 | 0.143 | 0.070 | 0.083 | 0.063 | 0.078 |
| 1.25 ug/mL | 2.153 | 0.060 | 1.149 | 0.148 | 0.071 | 0.085 | 0.076 | 0.074 |
| 0.625 ug/mL | 2.260 | 0.063 | 1.142 | 0.145 | 0.074 | 0.080 | 0.063 | 0.079 |
| 0.313 ug/mL | 2.162 | 0.056 | 0.994 | 0.148 | 0.071 | 0.079 | 0.060 | 0.075 |
| 0.156 ug/mL | 2.080 | 0.057 | 0.996 | 0.114 | 0.078 | 0.086 | 0.081 | 0.072 |
| 0.078 ug/mL | 1.823 | 0.056 | 0.877 | 0.112 | 0.075 | 0.069 | 0.064 | 0.067 |
| 0.039 ug/mL | 1.327 | 0.061 | 0.636 | 0.106 | 0.073 | 0.067 | 0.061 | 0.071 |
| 0.02 ug/mL | 0.898 | 0.059 | 0.440 | 0.097 | 0.069 | 0.066 | 0.070 | 0.065 |
| Blank | 0.078 | 0.065 | 0.069 | 0.071 | 0.079 | 0.068 | 0.062 | 0.069 |

Example 4

Identification of a Reactive Epitope

Ten peptide fragments of Bacillus GH were prepared and tested against the 23a-14G9 antibody. The fragments were synthesized by Mimotopes (Clayton Victoria Australia). The peptides included an "SGSG" linker and were biotinylated. The biotinylated peptides were immobilized onto streptavidin coated ELISA plates. A direct ELISA was performed utilizing dilutions of 23-14G9 monoclonal antibody.

The 10 peptides tested were as follows:

| | | |
|---|---|---|
| 1 | gtdwklpfkegnppa | (325-339 of SEQ ID NO: 1) |
| 2 | wklpfkegnppakai | (328-342 of SEQ ID NO: 1) |
| 3 | pfkegnppakaissv | (331-345 of SEQ ID NO: 1) |
| 4 | egnppakaissvaav | (334-248 of SEQ ID NO: 1) |
| 5 | ppakaissvaavala | (337-351 of SEQ ID NO: 1) |
| 6 | kaissvaavalarky | (340-354 of SEQ ID NO: 1) |
| 7 | ssvaavalarkynvp | (343-357 of SEQ ID NO: 1) |
| 8 | aavalarkynvpiry | (346-360 of SEQ ID NO: 1) |
| 9 | wklpfkegnppakaissvaa | (328-347 of SEQ ID NO: 1) |
| 10 | kegnppakaissvaavalar | (333-352 of SEQ ID NO: 1) |

Peptides 5, 6, and 10 were found to be reactive with the antibody.

All references cited herein, including patents, patent applications, and publications, are hereby incorporated by reference in their entireties, whether previously specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

---

What is claimed is:

1. An isolated antibody which binds glycosyl hydrolase on ungerminated *Bacillus* spores,
    wherein said glycosyl hydrolase has the sequence of SEQ ID NO: 1 or
    wherein said antibody binds a glycosyl hydrolase epitope comprising ISSVAAVALA (positions 342-351 of SEQ ID NO: 1).

2. The antibody of claim 1 wherein said *Bacillus* spores are spores of pathogenic and/or toxigenic *Bacilli*.

3. The antibody of claim 1 wherein said pathogenic and/or toxigenic *Bacillus* spores are spores of *B. anthracis, B. thuringiensis*, and *B. cereus*.

4. The antibody of claim 1 wherein said glycosyl hydrolase has the sequence of SEQ ID NO: 1.

5. A method of detecting the presence or absence of ungerminated *Bacillus* spores in a sample comprising
    detecting the binding of the antibody of claim 1 to said spores, after said antibody is contacted with said sample to allow formation of a complex of antibody bound spores.

6. The method of claim 5 wherein said *Bacillus* spores are spores of pathogenic and/or toxigenic *Bacilli*.

7. The method of claim 6 wherein said pathogenic and/or toxigenic *Bacillus* spores are spores of *B. anthracis, B. thuringiensis*, and *B. cereus*.

8. The method of claim 5 wherein said antibody binds a glycosyl hydrolase epitope comprising ISSVAAVALA (positions 342-351 of SEQ ID NO:1).

9. The method of claim 8 further comprising identifying said spores as spores of *B. anthracis*.

10. The method of claim 9 wherein said identifying comprises determining the spores as not spores of *B. thuringiensis* and/or *B. cereus*.

11. The method of claim 10 wherein said determining comprises detection of a *B. thuringiensis* and/or *B. cereus* specific epitope or *B. thuringiensis* and/or *B. cereus* nucleic acid sequence.

12. The method of claim 11 wherein said *B. thuringiensis* and/or *B. cereus* specific epitope is a glycosyl hydrolase epitope or
    said *B. thuringiensis* and/or *B. cereus* specific nucleic acid sequence encodes all or part of *Bacillus* glycosyl hydrolase.

13. The method of claim 5 wherein said antibody is detectably labeled or
    wherein said sample is suspected of containing *B. anthracis* spores.

14. The method of claim 5 wherein said complex comprises a capture reagent, optionally immobilized on a solid support.

15. The method of claim 14 wherein said capture reagent is another antibody, optionally polyclonal, that binds *Bacillus* spores, such as spores of *B. thuringiensis, B. cereus, B. pumilis, B. subtilis*, and *B. megaterium*.

16. A kit for detecting the presence or absence of *Bacillus* spores in a sample, said kit comprising the antibody of claim 1.

17. A complex comprising an antibody of claim 1 bound to a *Bacillus* spore.

18. The antibody of claim 1, wherein said antibody is a monoclonal antibody.

19. The antibody of claim 2, wherein said antibody is a monoclonal antibody.

20. The antibody of claim 3, wherein said antibody is a monoclonal antibody.

* * * * *

SEQUENCE LISTING

```
<160> NUMBER OF SEQ ID NOS: 8

<210> SEQ ID NO 1
<211> LENGTH: 430
<212> TYPE: PRT
<213> ORGANISM: Bacillus anthracis

<400> SEQUENCE: 1

Met Ile Gln Ile Val Thr Val Arg Ser Gly Asp Ser Val Tyr Ser Leu
1               5                   10                  15

Ala Ser Lys Tyr Gly Ser Thr Pro Asp Glu Ile Val Lys Asp Asn Gly
            20                  25                  30

Leu Asn Pro Ala Glu Thr Leu Val Val Gly Gln Ala Leu Ile Val Asn
        35                  40                  45

Thr Lys Gly Asn Asn Tyr Tyr Val Gln Pro Gly Asp Ser Leu Tyr Arg
    50                  55                  60

Ile Ser Gln Thr Tyr Asn Val Pro Leu Ala Ser Leu Ala Lys Val Asn
65                  70                  75                  80

Asn Leu Ser Leu Lys Ser Ile Leu His Val Gly Gln Gln Leu Tyr Ile
                85                  90                  95

Pro Lys Gly Thr Lys Arg Ala Val Glu Ser Ile Ala Tyr Leu Gln Pro
            100                 105                 110

Ser Thr Ile Pro Ile Lys Glu Ser Leu Val Asn Ala Thr Arg Ala Ile
        115                 120                 125

Asn Pro Phe Leu Thr Tyr Leu Ala Tyr Phe Ser Phe Glu Ala Lys Arg
    130                 135                 140

Asp Gly Thr Leu Lys Glu Pro Thr Glu Thr Ala Lys Ile Ala Asn Ile
145                 150                 155                 160
```

```
Ala Thr Gln Gly Asn Thr Ile Pro Met Leu Val Ile Thr Asn Ile Glu
            165                 170                 175

Asn Gly Asn Phe Ser Ala Asp Leu Thr Ser Val Ile Leu Arg Asp Ala
        180                 185                 190

Thr Ile Gln Asn Lys Phe Ile Thr Asn Ile Leu Gln Thr Ala Glu Lys
    195                 200                 205

Tyr Gly Met Arg Asp Ile His Phe Asp Phe Glu Ser Val Ala Pro Glu
210                 215                 220

Asp Arg Glu Ala Tyr Asn Arg Phe Leu Arg Asn Val Lys Thr Arg Leu
225                 230                 235                 240

Pro Ser Gly Tyr Thr Leu Ser Thr Leu Val Pro Lys Thr Ser Ser
            245                 250                 255

Asn Gln Lys Gly Lys Phe Phe Glu Thr His Asp Tyr Lys Ala Gln Gly
        260                 265                 270

Gln Ile Val Asp Phe Val Ile Met Thr Tyr Asp Trp Gly Trp Gln
    275                 280                 285

Gly Gly Pro Pro Met Ala Ile Ser Pro Ile Gly Pro Val Lys Glu Val
290                 295                 300

Leu Gln Tyr Ala Lys Ser Gln Met Pro Gln Lys Ile Met Met Gly
305                 310                 315                 320

Gln Asn Leu Tyr Gly Phe Asp Trp Lys Leu Pro Phe Lys Glu Gly Asn
            325                 330                 335

Pro Pro Ala Lys Ala Ile Ser Ser Val Ala Ala Val Ala Leu Ala Arg
        340                 345                 350

Lys Tyr Asn Val Pro Ile Arg Tyr Asp Phe Thr Ala Gln Ala Pro His
    355                 360                 365

Phe Asn Tyr Phe Asp Glu Asn Gly Val Gln His Glu Val Trp Phe Glu
370                 375                 380

Asp Ser Arg Ser Val Gln Ser Lys Phe Asn Leu Met Lys Glu Gln Gly
385                 390                 395                 400

Ile Gly Gly Ile Ser Tyr Trp Lys Ile Gly Leu Pro Phe Pro Gln Asn
            405                 410                 415

Trp Arg Leu Leu Val Glu Asn Phe Thr Ile Thr Lys Lys Gly
        420                 425                 430

<210> SEQ ID NO 2
<211> LENGTH: 430
<212> TYPE: PRT
<213> ORGANISM: Bacillus thuringiensis 97-27

<400> SEQUENCE: 2

Met Ile Gln Ile Val Thr Val Arg Ser Gly Asp Ser Val Tyr Ser Leu
1               5                   10                  15

Ala Ser Lys Tyr Gly Ser Thr Pro Asp Glu Ile Val Lys Asp Asn Gly
            20                  25                  30

Leu Asn Pro Ala Glu Thr Leu Val Val Gly Gln Ala Leu Ile Val Asn
        35                  40                  45

Thr Lys Gly Asn Asn Tyr Val Gln Pro Gly Asp Ser Leu Tyr Arg
    50                  55                  60

Ile Ser Gln Thr Tyr Asn Val Pro Leu Ala Ser Leu Ala Lys Val Asn
65                  70                  75                  80

Asn Leu Ser Leu Lys Ser Ile Leu His Val Gly Gln Gln Leu Tyr Ile
            85                  90                  95

Pro Lys Gly Thr Lys Arg Ala Val Glu Ser Ile Ala Tyr Leu Gln Pro
        100                 105                 110
```

```
Ser Thr Ile Pro Ile Lys Glu Ser Leu Val Asn Ala Thr Arg Ala Ile
        115                 120                 125

Asn Pro Phe Leu Thr Tyr Leu Ala Tyr Phe Ser Glu Ala Lys Arg
    130                 135                 140

Asp Gly Thr Leu Lys Glu Pro Thr Glu Thr Ala Lys Ile Ala Asn Ile
145                 150                 155                 160

Ala Thr Gln Gly Asn Thr Ile Pro Met Leu Val Ile Thr Asn Ile Glu
                165                 170                 175

Asn Gly Asn Phe Ser Ala Asp Leu Thr Ser Val Ile Leu Arg Asp Ala
                180                 185                 190

Thr Ile Gln Asn Lys Phe Ile Thr Asn Ile Leu Gln Thr Ala Glu Lys
            195                 200                 205

Tyr Gly Met Arg Asp Ile His Phe Asp Phe Glu Ser Val Ala Pro Glu
        210                 215                 220

Asp Arg Glu Ala Tyr Asn Arg Phe Leu Arg Asn Val Lys Thr Arg Leu
225                 230                 235                 240

Pro Ser Gly Tyr Thr Leu Ser Thr Thr Leu Val Pro Lys Thr Ser Ser
                245                 250                 255

Asn Gln Lys Gly Lys Phe Phe Glu Ala His Asp Tyr Lys Ala Gln Gly
                260                 265                 270

Gln Ile Val Asp Phe Val Val Ile Met Thr Tyr Asp Trp Gly Trp Gln
            275                 280                 285

Gly Gly Pro Pro Met Ala Ile Ser Pro Ile Gly Pro Val Lys Glu Val
        290                 295                 300

Leu Gln Tyr Ala Lys Ser Gln Met Pro Pro Gln Lys Ile Met Met Gly
305                 310                 315                 320

Gln Asn Leu Tyr Gly Phe Asp Trp Lys Leu Pro Phe Lys Glu Gly Asn
                325                 330                 335

Pro Pro Ala Lys Ala Ile Ser Ser Val Ala Ala Val Ala Leu Ala Arg
                340                 345                 350

Lys Tyr Asn Val Pro Ile Arg Tyr Asp Phe Thr Ala Gln Ala Pro His
            355                 360                 365

Phe Asn Tyr Phe Asp Glu Asn Gly Val Gln His Glu Val Trp Phe Glu
    370                 375                 380

Asp Ser Arg Ser Val Gln Ser Lys Phe Asn Leu Met Lys Glu Gln Gly
385                 390                 395                 400

Ile Gly Gly Ile Ser Tyr Trp Lys Ile Gly Leu Pro Phe Pro Gln Asn
                405                 410                 415

Trp Arg Leu Leu Val Glu Asn Phe Thr Ile Thr Lys Lys Gly
            420                 425                 430

<210> SEQ ID NO 3
<211> LENGTH: 430
<212> TYPE: PRT
<213> ORGANISM: Bacillus cereus E33L

<400> SEQUENCE: 3

Met Ile Gln Ile Val Thr Val Arg Ser Gly Asp Ser Val Tyr Ser Leu
1               5                   10                  15

Ala Ser Lys Tyr Gly Ser Thr Pro Asp Glu Ile Val Lys Asp Asn Gly
                20                  25                  30

Leu Asn Pro Ala Glu Thr Leu Val Gly Gln Ala Leu Ile Val Asn
            35                  40                  45

Thr Lys Gly Asn Asn Tyr Tyr Val Gln Pro Gly Asp Ser Leu Tyr Arg
        50                  55                  60
```

```
Ile Ser Gln Thr Tyr Asn Val Pro Leu Ala Ser Leu Ala Lys Val Asn
 65                  70                  75                  80

Asn Leu Ser Leu Lys Ser Ile Leu His Val Gly Gln Gln Leu Tyr Ile
                 85                  90                  95

Pro Lys Gly Thr Lys Arg Ala Val Glu Ser Ile Ala Tyr Leu Gln Pro
            100                 105                 110

Ser Thr Ile Pro Ile Lys Glu Ser Leu Val Asn Ser Thr Arg Ala Ile
        115                 120                 125

Asn Pro Phe Leu Thr Tyr Leu Ala Tyr Phe Ser Phe Glu Ala Lys Arg
    130                 135                 140

Asp Gly Thr Leu Lys Glu Pro Thr Glu Thr Ala Lys Ile Ala Asn Ile
145                 150                 155                 160

Ala Thr Gln Gly Asn Thr Ile Pro Met Leu Val Ile Thr Asn Ile Glu
                165                 170                 175

Asn Gly Asn Phe Ser Ala Asp Leu Thr Ser Val Ile Leu Arg Asp Ala
            180                 185                 190

Thr Ile Gln Asn Lys Phe Ile Thr Asn Ile Leu Gln Thr Ala Glu Lys
        195                 200                 205

Tyr Gly Met Arg Asp Ile His Phe Asp Phe Glu Ser Val Ala Pro Glu
    210                 215                 220

Asp Arg Glu Ala Tyr Asn Arg Phe Leu Arg Asn Val Lys Thr Arg Leu
225                 230                 235                 240

Pro Asn Gly Tyr Thr Leu Ser Thr Thr Leu Val Pro Lys Thr Ser Ser
                245                 250                 255

Asn Gln Lys Gly Lys Phe Phe Glu Ala His Asp Tyr Lys Ala Gln Gly
            260                 265                 270

Gln Ile Val Asp Phe Val Val Ile Met Thr Tyr Asp Trp Gly Trp Gln
        275                 280                 285

Gly Gly Pro Pro Met Ala Ile Ser Pro Ile Gly Pro Val Lys Glu Val
    290                 295                 300

Leu Gln Tyr Ala Lys Ser Gln Met Pro Pro Gln Lys Ile Met Met Gly
305                 310                 315                 320

Gln Asn Leu Tyr Gly Phe Asp Trp Lys Leu Pro Phe Lys Glu Gly Asn
                325                 330                 335

Pro Pro Ala Lys Ala Ile Ser Ser Val Ala Val Ala Leu Ala Arg
            340                 345                 350

Lys Tyr Asn Val Pro Ile Arg Tyr Asp Phe Thr Ala Gln Ala Pro His
        355                 360                 365

Phe Asn Tyr Phe Asp Glu Asn Gly Val Gln His Glu Val Trp Phe Glu
    370                 375                 380

Asp Ser Arg Ser Val Gln Ser Lys Phe Asn Leu Met Lys Glu Gln Gly
385                 390                 395                 400

Ile Gly Gly Ile Ser Tyr Trp Lys Ile Gly Leu Pro Phe Pro Gln Asn
                405                 410                 415

Trp Arg Leu Leu Val Glu Asn Phe Thr Ile Thr Lys Lys Gly
            420                 425                 430

<210> SEQ ID NO 4
<211> LENGTH: 430
<212> TYPE: PRT
<213> ORGANISM: Bacillus cereus 10987

<400> SEQUENCE: 4

Met Ile Gln Ile Val Thr Val Arg Ser Gly Asp Ser Val Tyr Ser Leu
 1               5                  10                  15
```

```
Ala Ser Lys Tyr Gly Ser Thr Pro Asp Glu Ile Val Lys Asp Asn Gly
         20                  25                  30

Leu Asn Pro Ala Glu Thr Leu Val Val Gly Gln Ala Leu Ile Val Asn
             35                  40                  45

Thr Lys Gly Asn Asn Tyr Tyr Val Gln Pro Gly Asp Ser Leu Tyr Arg
 50                  55                  60

Ile Ser Gln Thr Tyr Asn Val Pro Leu Ala Ser Leu Ala Lys Val Asn
 65                  70                  75                  80

Asn Leu Ser Leu Lys Ser Ile Leu His Val Gly Gln Gln Leu Tyr Ile
                 85                  90                  95

Pro Lys Gly Thr Lys Arg Ala Val Glu Ser Ile Ala Tyr Leu Gln Pro
            100                 105                 110

Ser Thr Ile Pro Ile Lys Glu Ser Leu Val Asn Ala Thr Arg Ala Ile
            115                 120                 125

Asn Pro Phe Leu Thr Tyr Leu Ala Tyr Phe Ser Phe Glu Ala Lys Arg
        130                 135                 140

Asp Gly Thr Leu Lys Glu Pro Thr Glu Thr Ala Lys Ile Ala Asn Ile
145                 150                 155                 160

Ala Thr Gln Gly Asn Thr Ile Pro Met Leu Val Ile Thr Asn Ile Glu
                165                 170                 175

Asn Gly Asn Phe Ser Ala Asp Leu Thr Ser Val Ile Leu Arg Asp Ala
            180                 185                 190

Thr Ile Gln Asn Lys Phe Ile Thr Asn Ile Leu Gln Thr Ala Glu Lys
        195                 200                 205

Tyr Gly Met Arg Asp Ile His Phe Asp Phe Glu Ser Val Ala Pro Glu
    210                 215                 220

Asp Arg Glu Ala Tyr Asn Arg Phe Leu Arg Asn Val Lys Thr Arg Leu
225                 230                 235                 240

Pro Asn Gly Tyr Thr Leu Ser Thr Thr Leu Val Pro Lys Thr Ser Ser
                245                 250                 255

Asn Gln Lys Gly Lys Phe Phe Glu Ala His Asp Tyr Lys Ala Gln Gly
            260                 265                 270

Gln Ile Val Asp Phe Val Val Ile Met Thr Tyr Asp Trp Gly Trp Gln
        275                 280                 285

Gly Gly Pro Pro Met Ala Ile Ser Pro Ile Gly Pro Val Lys Glu Val
    290                 295                 300

Leu Gln Tyr Ala Lys Ser Gln Met Pro Pro Gln Lys Ile Met Met Gly
305                 310                 315                 320

Gln Asn Leu Tyr Gly Phe Asp Trp Lys Leu Pro Phe Lys Gln Gly Asn
                325                 330                 335

Pro Pro Ala Lys Ala Val Ser Ser Val Ala Ala Val Ala Leu Ala Arg
            340                 345                 350

Lys Tyr Asn Val Pro Ile Arg Tyr Asp Phe Thr Ala Gln Ala Pro His
        355                 360                 365

Phe Asn Tyr Phe Asp Glu Asn Gly Val Gln His Glu Val Trp Phe Glu
    370                 375                 380

Asp Ala Arg Ser Ile Gln Ser Lys Phe Asn Leu Met Lys Glu Gln Gly
385                 390                 395                 400

Ile Gly Gly Ile Ser Tyr Trp Lys Ile Gly Leu Pro Phe Pro Gln Asn
                405                 410                 415

Trp Arg Leu Leu Val Glu Asn Phe Thr Ile Thr Lys Lys Gly
            420                 425                 430

<210> SEQ ID NO 5
```

<211> LENGTH: 430
<212> TYPE: PRT
<213> ORGANISM: Bacillus cereus G9241

<400> SEQUENCE: 5

```
Met Ile Gln Ile Val Thr Val Arg Ser Gly Asp Ser Val Tyr Ser Leu
1               5                   10                  15

Ala Ser Lys Tyr Gly Ser Thr Pro Asp Glu Ile Val Thr Asp Asn Gly
            20                  25                  30

Leu Asn Pro Ala Glu Thr Leu Val Gly Gln Ala Leu Ile Val Asn
        35                  40                  45

Thr Lys Gly Asn Asn Tyr Tyr Val Gln Pro Gly Asp Ser Leu Tyr Arg
50                  55                  60

Ile Ser Gln Thr Tyr Asn Val Pro Leu Ala Ser Leu Ala Lys Val Asn
65                  70                  75                  80

Asn Leu Ser Leu Lys Ser Ile Leu His Val Gly Gln Gln Leu Tyr Ile
                85                  90                  95

Pro Lys Gly Thr Lys Arg Ala Val Glu Ser Ile Ala Tyr Leu Gln Pro
            100                 105                 110

Ser Thr Ile Pro Ile Lys Glu Ser Leu Val Asn Ala Thr Arg Ala Ile
            115                 120                 125

Asn Pro Phe Leu Thr Tyr Leu Ala Tyr Phe Ser Phe Glu Ala Lys Arg
        130                 135                 140

Asp Gly Thr Leu Lys Glu Pro Thr Glu Thr Ala Lys Ile Ala Asn Ile
145                 150                 155                 160

Ala Thr Gln Gly Asn Thr Ile Pro Met Leu Val Ile Thr Asn Ile Glu
                165                 170                 175

Asn Gly Asn Phe Ser Ala Asp Leu Thr Ser Val Ile Leu Arg Asp Ala
            180                 185                 190

Thr Ile Gln Asn Lys Phe Ile Thr Asn Ile Leu Gln Thr Ala Glu Lys
        195                 200                 205

Tyr Gly Met Arg Asp Ile His Phe Asp Phe Glu Ser Val Ala Pro Glu
210                 215                 220

Asp Arg Glu Ala Tyr Asn Arg Phe Leu Arg Asn Val Lys Thr Arg Leu
225                 230                 235                 240

Pro Asn Gly Tyr Thr Leu Ser Thr Thr Leu Val Pro Lys Thr Ser Ser
                245                 250                 255

Asn Gln Lys Gly Lys Phe Phe Glu Ala His Asp Tyr Lys Ala Gln Gly
            260                 265                 270

Gln Ile Val Asp Phe Val Val Ile Met Thr Tyr Asp Trp Gly Trp Gln
        275                 280                 285

Gly Gly Pro Pro Met Ala Ile Ser Pro Ile Gly Pro Val Lys Glu Val
290                 295                 300

Leu Gln Tyr Ala Lys Ser Gln Met Pro Pro Lys Ile Met Met Gly
305                 310                 315                 320

Gln Asn Leu Tyr Gly Phe Asp Trp Lys Leu Pro Phe Lys Gln Gly Asn
                325                 330                 335

Pro Pro Ala Lys Ala Ile Ser Ser Val Ala Val Ala Leu Ala Arg
            340                 345                 350

Lys Tyr Asn Val Pro Ile Arg Tyr Asp Phe Thr Ala Gln Ala Pro His
        355                 360                 365

Phe Asn Tyr Phe Asp Glu Asn Gly Val Gln His Glu Val Trp Phe Glu
370                 375                 380

Asp Ser Arg Ser Val Gln Ser Lys Phe Asn Leu Met Lys Glu Gln Gly
385                 390                 395                 400
```

```
Ile Gly Gly Ile Ser Tyr Trp Lys Ile Gly Leu Pro Phe Pro Gln Asn
            405                 410                 415

Trp Arg Leu Leu Val Glu Asn Phe Thr Ile Thr Lys Lys Gly
            420                 425                 430

<210> SEQ ID NO 6
<211> LENGTH: 430
<212> TYPE: PRT
<213> ORGANISM: Bacillus cereus IFO 13597

<400> SEQUENCE: 6

Met Ile Gln Ile Val Thr Val Arg Ser Gly Asp Ser Val Tyr Ser Leu
1               5                   10                  15

Ala Ser Lys Tyr Gly Ser Thr Pro Asp Glu Ile Val Lys Asp Asn Gly
            20                  25                  30

Leu Asn Pro Ala Glu Thr Leu Val Gly Gln Ala Le

Lys Tyr Asn Val Pro Ile Arg Tyr Asp Phe Thr Ala Gln Ala Pro His
            355                 360                 365

Phe Asn Tyr Phe Asp Glu Asn Gly Val Gln His Glu Val Trp Phe Glu
        370                 375                 380

Asp Ser Arg Ser Val Gln Ser Lys Phe Asn Leu Met Lys Glu Gln Gly
385                 390                 395                 400

Ile Gly Gly Ile Ser Tyr Trp Lys Ile Gly Leu Pro Phe Pro Gln Asn
                405                 410                 415

Trp Arg Leu Leu Val Glu Asn Phe Thr Ile Thr Lys Lys Gly
            420                 425                 430

<210> SEQ ID NO 7
<211> LENGTH: 430
<212> TYPE: PRT
<213> ORGANISM: Bacillus cereus 14579

<400> SEQUENCE: 7

Met Ile Gln Ile Val Thr Val Arg Ser Gly Asp Ser Val Tyr Ser Leu
1               5                   10                  15

Ala Ser Lys Tyr Gly Ser Thr Pro Asp Glu Ile Val Lys Asp Asn Gly
            20                  25                  30

Leu Asn Pro Ala Glu Thr Leu Val Gly Gln Ala Leu Ile Val Asn
        35                  40                  45

Thr Lys Gly Asn Asn Tyr Tyr Val Gln Pro Gly Asp Ser Leu Tyr Arg
50                  55                  60

Ile Ser Gln Thr Tyr Asn Val Pro Leu Ala Ser Leu Ala Lys Val Asn
65                  70                  75                  80

Asn Leu Ser Leu Lys Ser Ile Leu His Val Gly Gln Gln Leu Tyr Val
            85                  90                  95

Pro Lys Gly Thr Lys Arg Thr Val Glu Ser Ile Ala Tyr Leu Gln Pro
        100                 105                 110

Ser Thr Ile Pro Ile Lys Glu Ser Leu Val Asn Ala Thr Arg Ala Ile
        115                 120                 125

Asn Pro Phe Leu Thr Tyr Leu Ala Tyr Phe Ser Phe Glu Ala Lys Arg
        130                 135                 140

Asp Gly Thr Leu Lys Glu Pro Thr Glu Thr Ala Lys Ile Ala Asn Ile
145                 150                 155                 160

Ala Thr Gln Gly Lys Thr Ile Pro Met Leu Val Ile Thr Asn Ile Glu
                165                 170                 175

Asn Gly Asn Phe Ser Ala Asp Leu Thr Ser Val Ile Leu Arg Asp Ala
            180                 185                 190

Thr Ile Gln Asn Lys Phe Ile Thr Asn Ile Leu Gln Thr Ala Gln Lys
        195                 200                 205

Tyr Gly Met Arg Asp Ile His Phe Asp Phe Glu Ser Val Ala Pro Glu
    210                 215                 220

Asp Arg Glu Ala Tyr Asn Arg Phe Leu Arg Asn Val Lys Thr Arg Leu
225                 230                 235                 240

Pro Ser Gly Tyr Thr Leu Ser Thr Leu Val Pro Lys Thr Ser Ser
                245                 250                 255

Asn Gln Lys Gly Lys Phe Phe Glu Ala His Asp Tyr Lys Ala Gln Gly
            260                 265                 270

Gln Ile Val Asp Phe Val Val Ile Met Thr Tyr Asp Trp Gly Trp Gln
        275                 280                 285

Gly Gly Pro Pro Met Ala Ile Ser Pro Ile Gly Pro Val Lys Glu Val
    290                 295                 300

```
Leu Gln Tyr Ala Lys Ser Gln Met Pro Pro Gln Lys Ile Met Met Gly
305                 310                 315                 320

Gln Asn Leu Tyr Gly Phe Asp Trp Lys Leu Pro Phe Lys Gln Gly Asn
                325                 330                 335

Pro Pro Ala Lys Ala Ile Ser Ser Val Ala Ala Val Thr Leu Ala Arg
            340                 345                 350

Lys Tyr Asn Val Pro Ile Arg Tyr Asp Phe Thr Ala Gln Ala Pro His
        355                 360                 365

Phe Asn Tyr Phe Asp Glu Asn Gly Val Gln His Glu Val Trp Phe Glu
370                 375                 380

Asp Ser Arg Ser Val Gln Ser Lys Phe Asn Leu Met Lys Glu Gln Gly
385                 390                 395                 400

Ile Gly Gly Ile Ser Tyr Trp Lys Ile Gly Leu Pro Phe Pro Gln Asn
                405                 410                 415

Trp Arg Leu Leu Val Glu Asn Phe Thr Ile Thr Lys Lys Gly
            420                 425                 430

<210> SEQ ID NO 8
<211> LENGTH: 220
<212> TYPE: PRT
<213> ORGANISM: Bacillus thuringiensis serovar israelensis

<400> SEQUENCE: 8

Met Arg Asp Ile His Phe Asp Phe Glu Ser Val Ala Pro Glu Asp Arg
1               5                   10                  15

Glu Ala Tyr Asn Arg Phe Leu Arg Asn Val Lys Thr Arg Leu Pro Ser
            20                  25                  30

Gly Tyr Thr Leu Ser Thr Thr Leu Val Pro Lys Thr Ser Ser Asn Gln
        35                  40                  45

Lys Gly Lys Phe Phe Glu Ala His Asp Tyr Lys Ala Gln Gly Gln Ile
    50                  55                  60

Val Asp Phe Val Val Ile Met Thr Tyr Asp Trp Gly Trp Gln Gly Gly
65                  70                  75                  80

Pro Pro Met Ala Ile Ser Pro Ile Gly Pro Val Lys Glu Val Leu Gln
                85                  90                  95

Tyr Ala Lys Ser Gln Met Pro Pro Gln Lys Ile Met Met Gly Gln Asn
            100                 105                 110

Leu Tyr Gly Phe Asp Trp Lys Leu Pro Phe Lys Gln Gly Asn Pro Pro
        115                 120                 125

Ala Lys Ala Ile Ser Ser Val Ala Ala Val Ala Leu Ala Arg Lys Tyr
    130                 135                 140

Asn Val Pro Ile Arg Tyr Asp Phe Thr Ala Gln Ala Pro His Phe Asn
145                 150                 155                 160

Tyr Phe Asp Glu Asn Gly Val Gln His Glu Val Trp Phe Glu Asp Ser
                165                 170                 175

Arg Ser Val Gln Ser Lys Phe Asn Leu Met Lys Glu Gln Gly Ile Gly
            180                 185                 190

Gly Ile Ser Tyr Trp Lys Ile Gly Leu Pro Phe Pro Gln Asn Trp Arg
        195                 200                 205

Leu Leu Val Glu Asn Phe Thr Ile Thr Lys Lys Gly
    210                 215                 220
```